(12) United States Patent
McNeal (10) Patent No.: US 9,072,331 B2
(45) Date of Patent: Jul. 7, 2015

(54) GOGGLE ATTACHMENT SYSTEM FOR A HELMET

(75) Inventor: Joseph R. McNeal, Hailey, ID (US)

(73) Assignee: Smith Optics, Inc., Ketchum, ID (US)

( * ) Notice: Subject to any disclaimer, the term of this patent is extended or adjusted under 35 U.S.C. 154(b) by 334 days.

(21) Appl. No.: 13/007,875

(22) Filed: Jan. 17, 2011

(65) Prior Publication Data

US 2012/0180202 A1     Jul. 19, 2012

(51) Int. Cl.
  *A42B 1/24*     (2006.01)
  *A42B 3/18*     (2006.01)
  *A61F 9/02*     (2006.01)

(52) U.S. Cl.
  CPC  *A42B 3/185* (2013.01); *A61F 9/027* (2013.01)

(58) Field of Classification Search
  CPC ............ A42B 3/185; A42B 3/04; A42B 3/18; A42B 1/247; G02C 3/02; G02C 9/04; A61F 9/027
  USPC .............. 2/6.3, 6.5, 6.7, 9, 10, 421, 422, 424, 2/426, 432, 438, 439, 448, 450, 452, 453, 2/909
  See application file for complete search history.

(56) References Cited

U.S. PATENT DOCUMENTS

| | | | |
|---|---|---|---|
| 860,322 A * | 7/1907 | Paroubek | ............................ 2/10 |
| 2,804,623 A | 9/1957 | Hirschmann | |
| 2,903,700 A | 9/1959 | Finken et al. | |
| 3,216,023 A * | 11/1965 | Morgan | ................................ 2/9 |
| 3,237,203 A | 3/1966 | Nielsen | |
| D213,085 S | 1/1969 | Wyckoff | |
| 3,691,565 A | 9/1972 | Galonek | |
| 3,783,452 A * | 1/1974 | Benson et al. | ...................... 2/6.4 |
| 4,042,974 A * | 8/1977 | Morgan et al. | ........................ 2/9 |
| 4,136,403 A * | 1/1979 | Walther et al. | ...................... 2/10 |
| D266,626 S | 10/1982 | Gooding | |
| 4,527,291 A | 7/1985 | Finken et al. | |

(Continued)

FOREIGN PATENT DOCUMENTS

FR         2838307 A1 * 10/2003 ............... A42B 3/18
JP      2000-239916 A     9/2000

(Continued)

OTHER PUBLICATIONS

English Machine Translation of FR 2838307 A1 via http://www.espacenet.com (generated on Apr. 11, 2013).*

(Continued)

*Primary Examiner* — Alissa L Hoey
*Assistant Examiner* — Jameson Collier
(74) *Attorney, Agent, or Firm* — Dorsey & Whitney LLP (57) ABSTRACT

Goggles, goggle attachment systems, and helmets are described. One such goggle attachment system includes an attachment post and a resilient goggle strap tab. The attachment post includes a post portion and a stop and the goggle strap tab includes an opening. The goggle strap tab is configured to be stretched and the opening pulled over the stop and onto to the post portion. The goggle strap tab is retained on the post portion by the stop. An example goggle includes a frame, a resilient strap attached to the frame, and a resilient goggle strap tab attached to the strap. The goggle strap tab having an opening disposed between a strap tab and a tab pull. The goggle strap tab is configured to stretch when pulled by the tab pull along a longitudinal axis and the opening being asymmetrical about an axis substantially perpendicular to the longitudinal axis when stretched.

17 Claims, 10 Drawing Sheets

(56) References Cited

U.S. PATENT DOCUMENTS

| | | | |
|---|---|---|---|
| 4,686,712 A | 8/1987 | Spiva | 2/10 |
| 4,713,844 A | 12/1987 | Westgate | |
| 4,716,601 A | 1/1988 | Nussbickl | |
| 4,764,989 A | 8/1988 | Bourgeois | |
| 4,918,753 A | 4/1990 | Mermillod | |
| 5,363,512 A | 11/1994 | Grabos et al. | |
| 5,410,763 A | 5/1995 | Bolle | |
| D372,928 S | 8/1996 | Brune et al. | |
| 5,592,698 A | 1/1997 | Woods | |
| 5,689,834 A | 11/1997 | Wilson | |
| 5,760,867 A | 6/1998 | Pernicka et al. | |
| D400,555 S | 11/1998 | Wang | |
| 5,845,341 A * | 12/1998 | Barthold et al. | 2/424 |
| 5,867,841 A | 2/1999 | Chiang | |
| 5,987,652 A | 11/1999 | Fowler | |
| 6,047,410 A | 4/2000 | Dondero | |
| D428,906 S | 8/2000 | Bolle | |
| 6,276,795 B1 | 8/2001 | Hall et al. | |
| D455,522 S | 4/2002 | Royes et al. | |
| D464,174 S | 10/2002 | Lu | |
| 6,490,729 B1 * | 12/2002 | Dondero | 2/10 |
| D477,010 S | 7/2003 | Moritz et al. | |
| D482,500 S | 11/2003 | Ho | |
| 6,708,340 B1 | 3/2004 | Dondero | |
| 6,715,157 B2 * | 4/2004 | Mage | 2/439 |
| 6,845,548 B1 * | 1/2005 | Lin | 24/265 BC |
| 6,970,691 B2 | 11/2005 | Thompson | |
| D515,615 S | 2/2006 | Fecteau et al. | |
| D535,059 S | 1/2007 | Lam | |
| 7,260,850 B2 * | 8/2007 | Ambuske et al. | 2/6.3 |
| D556,951 S | 12/2007 | Gath | |
| D610,602 S | 2/2010 | Yun | |
| D616,915 S | 6/2010 | Silveria et al. | |
| D628,346 S | 11/2010 | Petzl | |
| D645,210 S | 9/2011 | Chilson et al. | |
| D675,249 S | 1/2013 | Giroux | |
| D698,854 S | 2/2014 | McNeal | |
| D700,929 S | 3/2014 | McNeal | |
| D710,930 S | 8/2014 | McNeal | |
| 2005/0183190 A1 * | 8/2005 | Hussey | 2/424 |
| 2006/0059606 A1 | 3/2006 | Ferrara | |
| 2007/0083967 A1 * | 4/2007 | Crossman et al. | 2/15 |
| 2007/0130672 A1 | 6/2007 | Beddoe et al. | |
| 2008/0052808 A1 | 3/2008 | Leick et al. | |
| 2008/0172778 A1 | 7/2008 | Lysogorski | |
| 2008/0256688 A1 | 10/2008 | Bruce | |
| 2008/0301857 A1 | 12/2008 | Wang-Lee | |
| 2008/0301858 A1 | 12/2008 | Wang-Lee | |
| 2009/0268153 A1 | 10/2009 | Wang-Lee | |
| 2009/0300830 A1 | 12/2009 | Mage | |
| 2010/0064421 A1 | 3/2010 | Wang-Lee | |
| 2010/0325784 A1 | 12/2010 | Abbott et al. | |
| 2011/0072564 A1 * | 3/2011 | Krauter | 2/422 |
| 2011/0113535 A1 * | 5/2011 | Lebel et al. | 2/422 |
| 2011/0258759 A1 | 10/2011 | Renaud-Goud et al. | |
| 2011/0265237 A1 | 11/2011 | Lazar et al. | |
| 2012/0180203 A1 * | 7/2012 | Giroux et al. | 2/422 |
| 2012/0185989 A1 * | 7/2012 | Higgins | 2/15 |
| 2013/0019387 A1 | 1/2013 | McNeal | |
| 2014/0115761 A1 | 5/2014 | McNeal et al. | |

FOREIGN PATENT DOCUMENTS

| | | |
|---|---|---|
| KR | 10-0918879 B1 | 9/2009 |
| WO | 2008/006357 A2 | 1/2008 |
| WO | 2009/092368 A2 | 7/2009 |
| WO | 2010/076817 A1 | 7/2010 |
| WO | 2012/099631 A1 | 7/2012 |

OTHER PUBLICATIONS

International Search Report and Written Opinion dated May 23, 2012 for PCT Application No. PCT/US2011/055726.

Office action dated Apr. 24, 2015 issued for Canadian Appln No. 2,843,692.

* cited by examiner

GOGGLE ATTACHMENT SYSTEM FOR A HELMET

TECHNICAL FIELD

Embodiments of the invention relate generally to goggles and helmets, and more specifically, in one or more of the illustrated embodiments, to goggle attachment systems for attaching a goggle to a helmet.

BACKGROUND OF THE INVENTION

Protective gear may be worn to protect the person from injury during participation in an activity. In the case of helmets and goggles, the two are often worn together to protect the wearer's head and eyes from injury. Goggles are often designed to be worn with helmets, and vice versa, due to the frequency of the two being worn together. For example, helmets may include a mechanism for clipping the goggle strap to the rear portion of a helmet so that even if the goggles are displaced, the goggle strap remains clipped to the helmet.

Although the mechanism can prevent the goggles from being lost, when the goggles are resting on the front of the helmet, for example, when the goggles are not in use, and the strap is clipped into the mechanism, there is a tendency for the strap to pull the goggles up over the crown and off the helmet to be left dangling from the clipped-in strap. To return the goggles to the front of the helmet or put the goggles on the wearer's face requires finding the goggles as they are hanging from the rear of the helmet. Trying to grab the goggles when they are in this position may be inconvenient and difficult given that this often occurs when the wearer of the helmet is also wearing gloves and heavy protective gear.

Additionally, attaching and detaching the goggles from the helmet when the strap is clipped-in may also take more effort than desirable because the clips are designed to prevent the goggles from accidentally detaching from the helmet. Detaching the goggles requires the strap to be unclipped, which may involve the wearer removing the helmet in order to view the rear portion of the helmet to unclip the strap.

Therefore, it may be desirable to have a goggle attachment system for a helmet that provides easy attachment and detachment of goggles, and may allow goggles to be positioned on the helmet when, for example, the goggles are not in use.

DETAILED DESCRIPTION

The present application describes a goggle attachment system and a method of attaching goggles to a helmet. Many specific details of certain embodiments of the invention are set forth in the following description and the Figures provide a thorough understanding of such embodiments. One skilled in the art, however, will understand that the present invention may have additional embodiments and that other embodiments of the invention may be practiced without several of the details and components described in the following description.

Figure 1A:
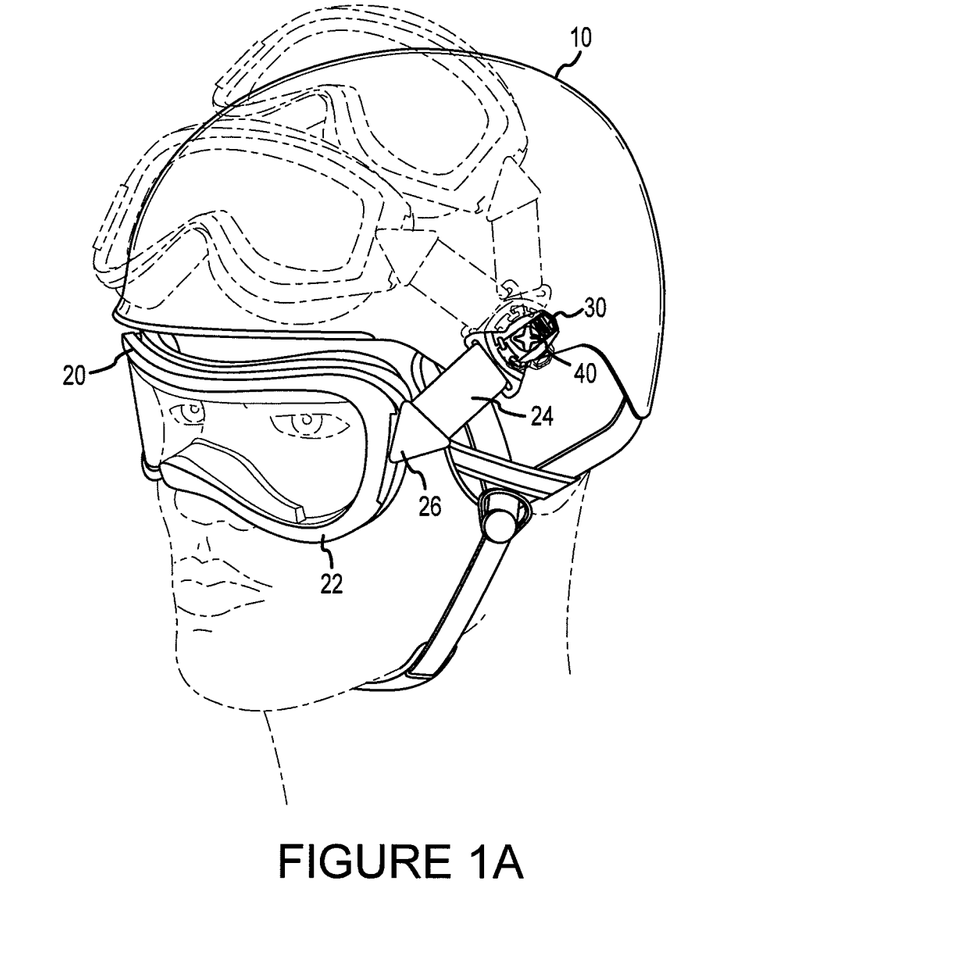
FIGS. 1A and 1B are drawings of a goggle attachment system according to an embodiment of the invention for a helmet.
Figure 1B:
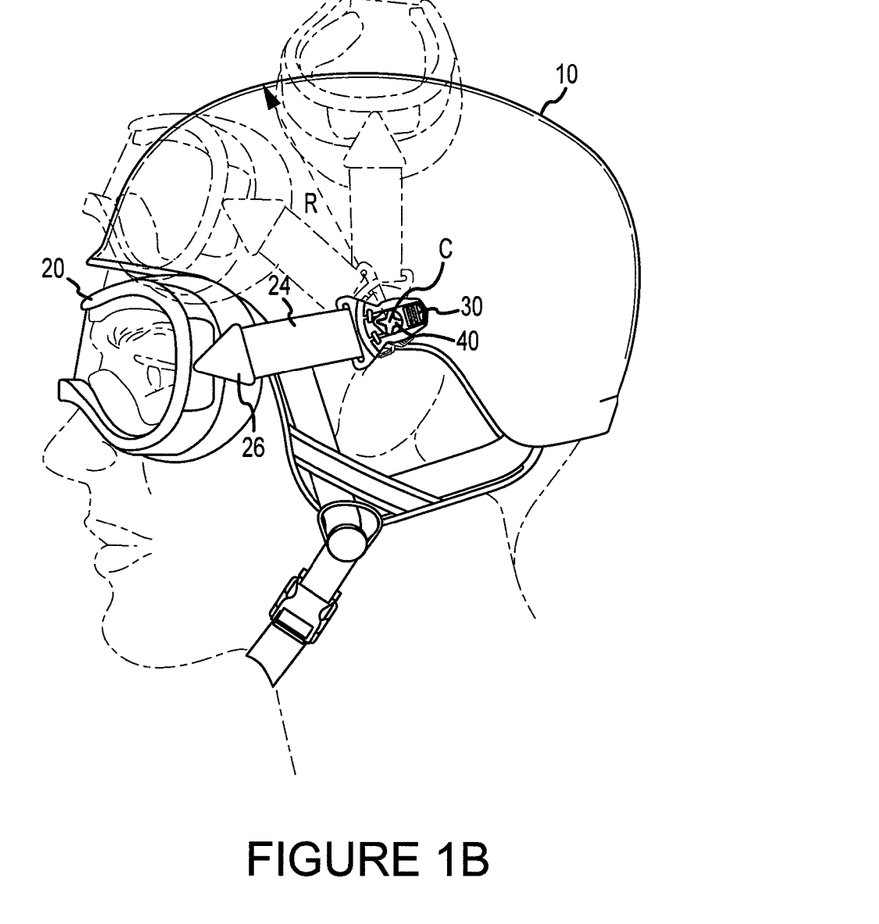
Figure 2A:
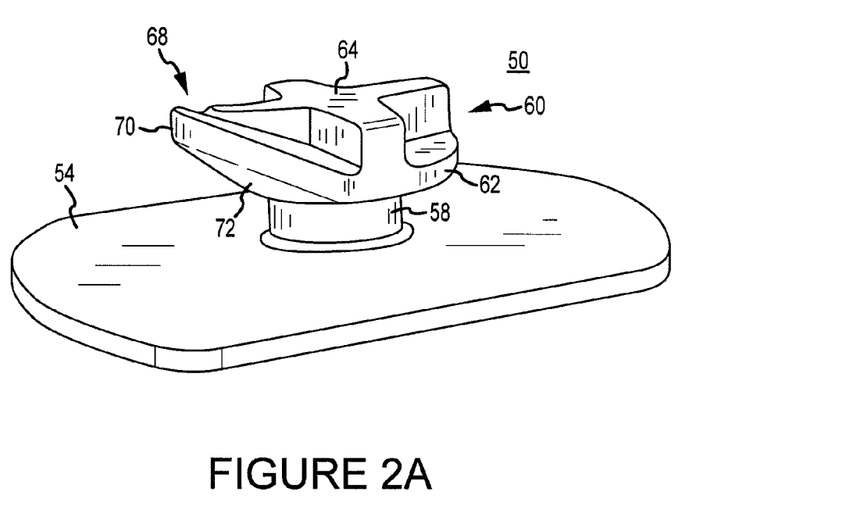
FIGS. 2A, 2B, 2C, and 2D are drawings of an attachment post according to an embodiment of the invention for a goggle attachment system for a helmet.
Figure 2B:
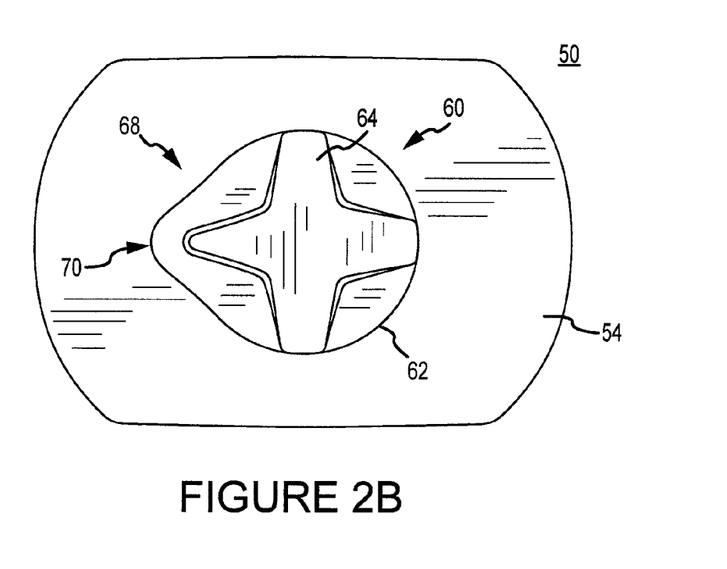
Figure 2C:
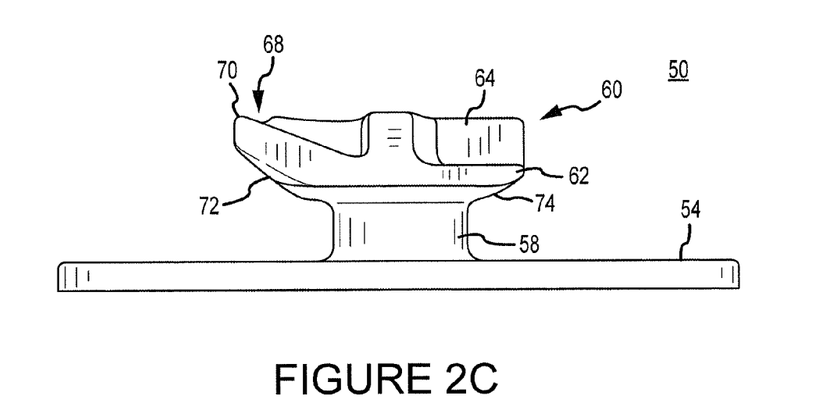
Figure 2D:
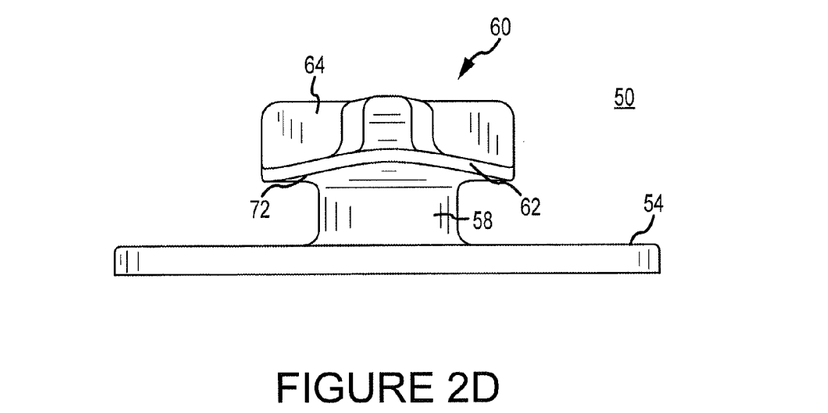

FIGS. 1A and 1B illustrate a goggle attachment system for a helmet 10 according to an embodiment of the invention. Goggles 20 have a frame 22 to which resilient strap 24 is attached by strap connectors 26. A second resilient strap 24 and strap connector 26 (both not shown) are attached to the opposite side of the frame of the goggles. The strap connectors 26 may be pivotally attached to the frame of the goggles 20, as shown in the embodiment of FIGS. 1A and 1B. A pivotal attachment of the strap connectors 26 to the goggles 20 has a benefit of allowing for the straps to pivot and achieve an angle relative to the frame of the goggles 20 to comfortably position the goggles 20 on a variety of face shapes and avoid strap binding. Other attachment techniques may be used as well without departing from the scope of the present invention. A strap tab 30 attached to the strap 24 is positioned on an attachment post 40 that is attached to the helmet 10. The strap tab 30 may be attached to the strap 24 using conventional techniques. As will be described in more detail below, the strap tab 30 may be resilient so that it may be pulled onto and off the post 40 to facilitate the goggles 20 being attached to or detached from the helmet 10. In some embodiments, another post 40 (not shown) is positioned on an opposite side of the helmet 10 to which a second strap tab 30 attached to a second strap 24 may be pulled onto and off.

In some embodiments, the post 40 may be positioned approximately at a center C of a general radius R of the outside surface of the helmet 10. With the post 40 positioned at C, the goggles 20 may be rotated to various positions on the outside surface of the helmet 10, a shown in FIGS. 1A and 1B, without the straps 24 tending to pull the goggles 20 to an undesirable position on the helmet 10, such as may be the case where the straps 24 are attached proximate a rear portion of the helmet 10. Posts 40, however, may be attached to the helmet 10 at different locations on the helmet 10 without departing from the scope of the invention.

FIGS. 2A, 2B, 2C, and 2D illustrate various views of an attachment post 50 according to an embodiment of the invention. The post 50 may be used as the post 40 in FIGS. 1A and 1B. The post 50 has a base 54 from which a post portion 58 extends. A stop 60 is positioned on the post portion 58. The stop 60 has a lateral dimension that is generally larger than the lateral dimension of the post portion 58. For example, as shown in FIGS. 2A, 2B, 2C, and 2D, the general diameter of the stop 60 is greater than the diameter of the post portion 58. The stop 60 includes a hook portion 68 and a rounded pullover portion 62. The hook portion 68 includes tapered portions that form a nose 70 and a sloped portion 72 that slopes from the post portion 58 toward the nose 70. A reinforcement structure 64 may be formed on the stop 60 to provide additional strength to the stop 60. In the embodiment shown in FIGS. 2A, 2B, 2C, and 2D the reinforcement structure 64 is formed from intersecting perpendicular ridges formed on the stop 60. A ramp portion 74 extends from the post 50 to under the rounded pullover portion 62. As will be described in more detail below, a strap tab, for example, strap tab 30 of FIGS. 1A and 1B, may be pulled onto and over the stop 60 and onto the attachment post 50. The stop 60 is configured to retain the strap tab on the post portion 58. The attachment post 50 may be mounted to a helmet by the base 54, for example, using an adhesive material. In some embodiments, the attachment post 50 may be integrated with the helmet. The attachment post 50 may be formed with a base 54 having a configuration that fits into a receiver mounted on a helmet, for example, a slot or rail in other embodiments. The attachment post 50 may also be attached to a helmet using other techniques now known or later developed without departing from the scope of the present invention.

Figure 3A:
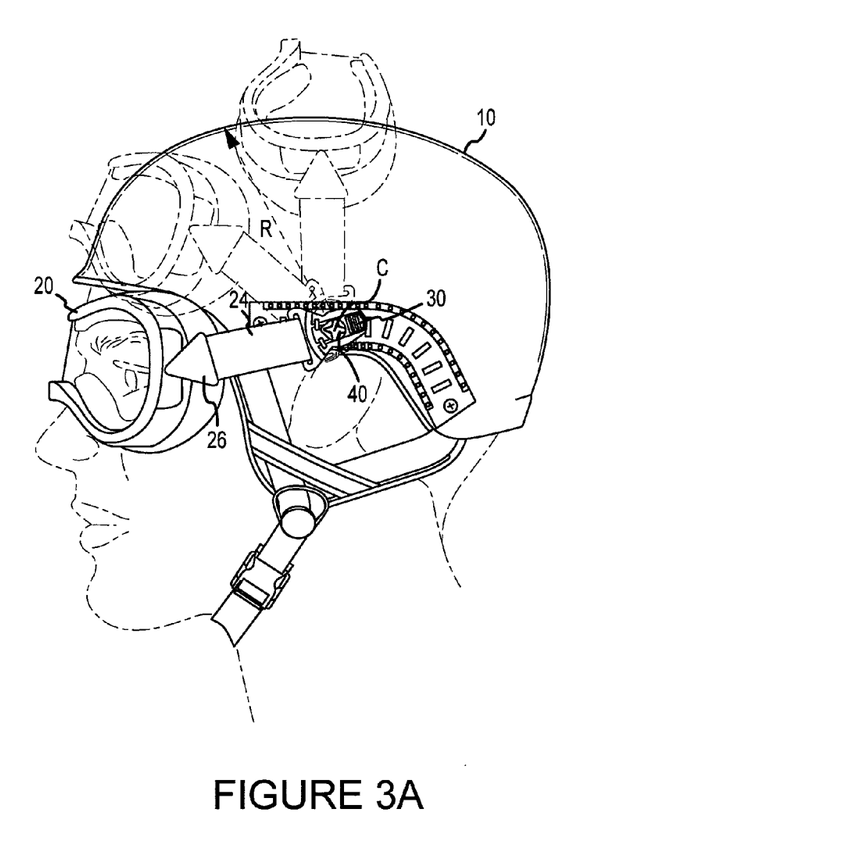
FIGS. 3A, 3B, and 3C are drawings of a goggle attachment system according to another embodiment of the invention.
Figure 3B:
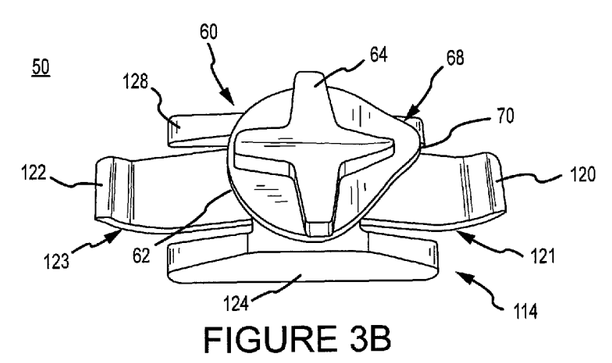
Figure 3C:
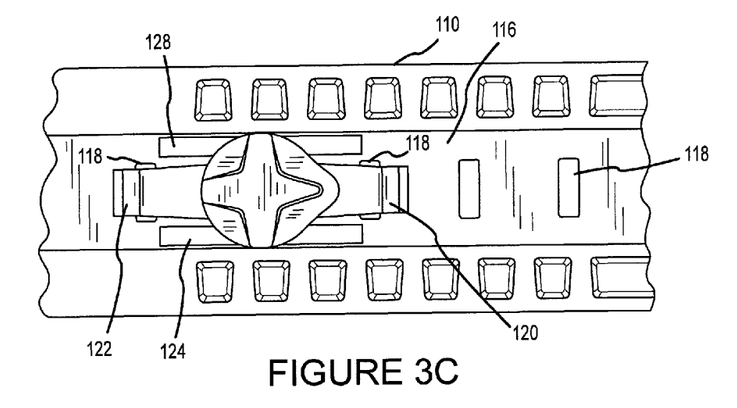

FIG. 3A illustrates a goggle attachment system for a helmet 10 according to an embodiment of the invention. Goggles 20 are attached to the helmet 10 by strap connectors 26 positioned on attachment post 50. The attachment post 50 is slidably attached to rail 110, which is secured to the helmet 10, for example, by fasteners 112. The rail 110 may allow for the post 50 to be moved along the rail, and may also provide an attachment mechanism for other devices. FIGS. 3B and 3C illustrate an attachment post 50 and rail 110 according to an embodiment of the invention. The attachment post 50 includes a stop 60 positioned on a post portion (not shown in FIGS. 3A-3C). As with the embodiment of FIGS. 2A-2D, the stop 60 has a lateral dimension that is generally larger than the lateral dimension of the post portion, for example, the diameter of the stop 60 is greater than the diameter of the post portion. In the embodiment of FIGS. 3B and 3C, the configuration of the stop 60 and the post portion are the same as that for the embodiment of FIGS. 2A-2D.

In contrast, however, the post portion and stop 60 extend from a base 114 that fits within a channel 116. The base 114 includes channel guides 124, 128 that are configured to retain the post 50 in the channel 116 and allow it to slide in the channel 116 without much lateral movement or twisting of the post. The base 114 further includes resilient clips 120, 122 having ridges 121, 123, respectively, that may engage slots 118 to hold the attachment post 50 in place in the channel 116. To slide the attachment post 50 in the channel 116, the attachment post 50 may be released by lifting the resilient clips 120, 122 to disengage the ridges 121, 123 from the slots 118 so that it may be free to slide. The resilient clips 120, 122 can be released to allow the ridges 121, 123 to engage slots 118 corresponding to the new position.

Figure 4A:
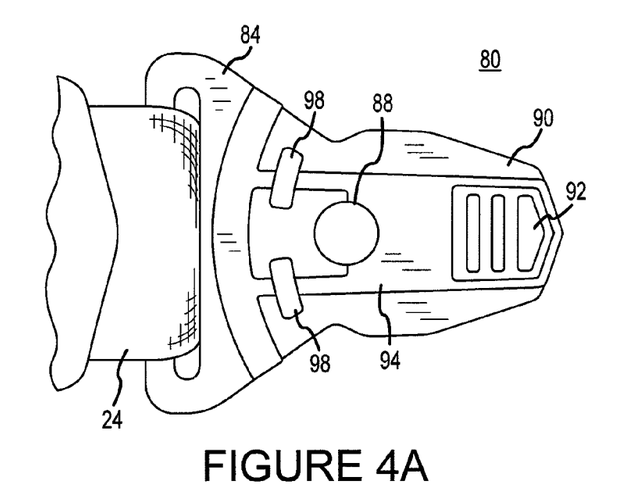
FIGS. 4A, 4B, and 4C are drawings of goggle strap tab according to an embodiment of the invention for a goggle attachment system for a helmet.
Figure 4B:
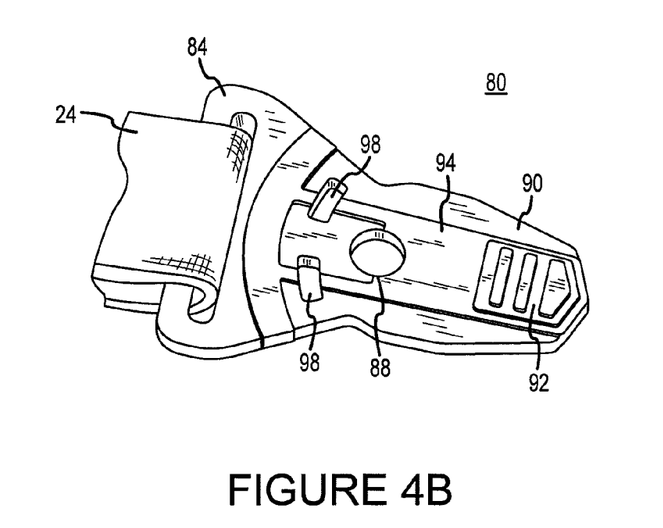
Figure 4C:
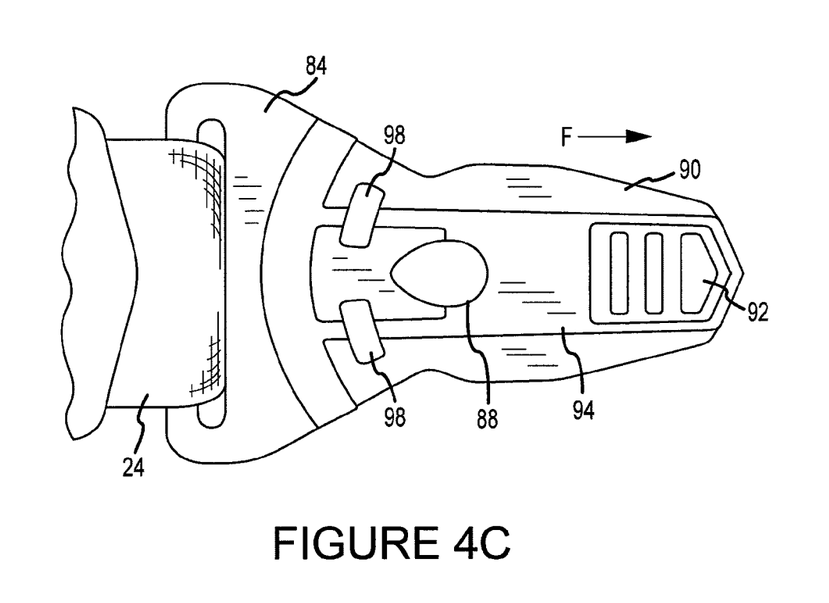

FIGS. 4A, 4B, and 4C illustrate a goggle strap tab 80 according to an embodiment of the invention. The strap tab 80 may be used as the strap tab 30 if FIGS. 1A and 1B. The strap tab 80 is formed from a resilient material, for example, so that the strap tab 80 may be stretched by pulling and return to its unstretched shape without permanent deformation. The strap tab 80 includes a loop portion 84 through which a strap 24 may be fitted for attachment to the strap tab 80. An opening 88 in the strap tab 80 is configured to be pulled onto an attachment post, for example, attachment post 40, to secure the strap tab 80 thereon. A tab pull 90 is formed with a grip 92 to facilitate gripping of the tab pull 90. As will be described in more detail below, the tab pull 90 may be gripped at the grip 92 for pulling the strap tab 80 when attaching or detaching the strap tab 80 to or from the attachment post. In some embodiments, the grip 92 is formed from alternating raised portions, for example, as shown in FIGS. 4A-4C. In some embodiments, alternating recessed portions may be used to form the grip 92.

Reinforcement ridge portion 94 is formed on the strap tab 80 to reinforce the strap tab 80 when it is pulled during attachment and detachment. Relief portion 98 may be formed in the strap tab 80, for example, for the embodiment illustrated by FIGS. 4A-4C, by forming an opening through the strap tab 80. In some embodiments, the reinforcement ridge portion 94 and/or relief portions 98 are configured to influence the shape of the opening 88 when the strap tab 80 is pulled and stretched. For example, in the embodiment shown in FIG. 4C, a force F is applied to the strap tab 80, for example, by pulling on the tab pull 90, and the resulting shape of the opening 88 is a "teardrop" with the narrower portion on the side opposite of tab pull 90 and a rounded portion proximate the tab pull 90.

Figure 5A:
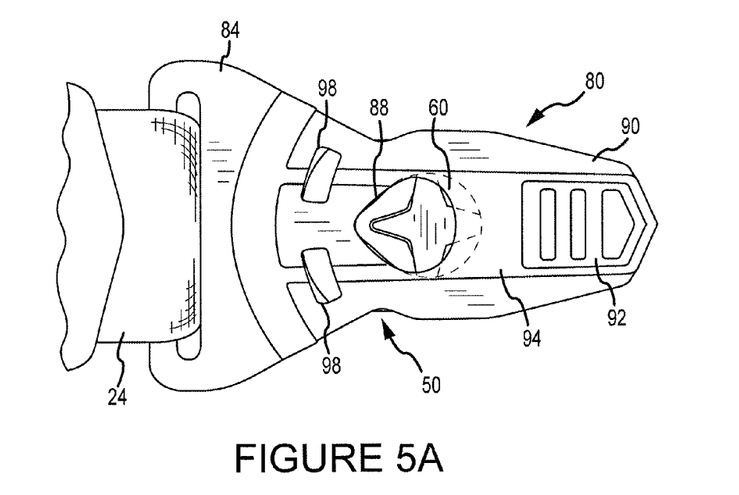
FIGS. 5A and 5B are drawings of the goggle strap tab of FIGS. 4A and 4B being pulled over and onto the attachment post of FIG. 2A-2D or 3A-3C.
Figure 5B:
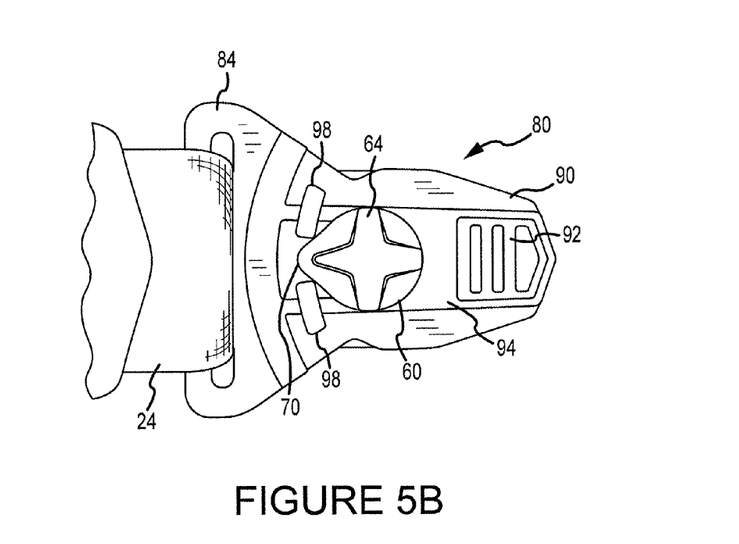
Figure 5C:
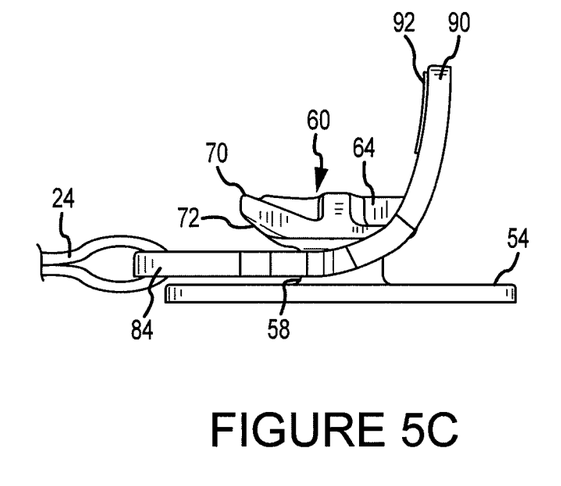
FIG. 5C is a drawing of the goggle strap tab of FIGS. 4A and 4B being pulled over and off the attachment post of FIG. 2A-2D or 3A-3C.

FIGS. 5A and 5B illustrate an embodiment where the goggle strap tab 80 of FIGS. 4A and 4B is being pulled over and onto the attachment post 50 of FIG. 2A-2D or 3A-3C. FIG. 5C illustrates an embodiment of the invention where the goggle strap tab 80 is being pulled over and off the attachment post 50.

The goggle strap tab 80 is attached to the attachment post 50 by pulling the goggle strap tab 80 over the stop 60 and onto the post portion 58 of the attachment post 50. A portion of the opening 88 (e.g., opposite of the tab pull 90) is positioned with the nose 70 of the hook portion 64 partially extending therethrough and a force F is applied to the tab pull 90. With the opening 88 held on the hook portion 68, the force F causes the strap tab 80 to stretch (FIG. 5A). As the tab pull 90 is pulled further, the opening 88 is spread open by the tapered portions of the hook portion 68 so that the opening 88 may be drawn over the rounded portion of the stop 60 and the tapered portion causes the opening 88 opposite of the tab pull 90 to slide onto the post portion 58. With the portion of opening 88 proximate the tab pull 90 drawn over the rounded portion of stop 60, the tab pull 90 may be released to fully position the goggle strap tab 80 on the post portion 64 (FIG. 5B).

The goggle strap tab 80 is detached from the attachment post 50 by pulling the portion of the opening 88 proximate the tab pull 90 off the post portion 58 and over the rounded portion of the stop 60. A force F is applied to the tab pull 90 to stretch the goggle strap tab 80 and cause the ramp portion 74 of the stop 60 to expand the opening 88 (FIG. 5C). As the force F is continued to be applied, the opening 88 expands sufficiently to come off the post portion 58 and over the stop 60. The tab pull 90 may be released when a portion of the opening 88 pulled over the stop 60. The opening 88 contracts due to the resiliency of the goggle strap tab 80, which slides off the hook portion 68 of the stop 60 so that the goggle strap tab 80 is fully detached from the attachment post 50.

From the foregoing it will be appreciated that, although specific embodiments of the invention have been described herein for purposes of illustration, various modifications may be made without deviating from the spirit and scope of the invention. Accordingly, the invention is not limited except as by the appended claims. Accordingly, the invention is not limited except as by the appended claims.

What is claimed is:

1. A goggle attachment system for a helmet, comprising:
an attachment post including a post portion and a stop, the stop including a hook portion and a rounded pullover portion opposite the hook portion, the stop oriented wherein the hook portion is configured to point towards a front of the helmet and the rounded pullover portion is configured to point towards a rear of the helmet, the hook portion including tapered portions extending rectilinearly from the rounded pullover portion to a nose, the hook portion further including a sloped portion that slopes from the nose towards the post portion along a surface of the stop adjacent to the post portion, the stop further including a ramp portion between the post portion and the rounded pullover portion along the surface of the stop adjacent to the post portion, wherein the hook portion and the rounded pullover portion are asymmetric to each other about an axis that divides the hook portion from the rounded pullover portion; and a goggle strap tab including an opening, the goggle strap tab configured to allow the stop to pass through the opening to secure the goggle strap tab to the post portion of the attachment post, the goggle strap tab retained on the post portion by the stop.

2. The goggle attachment system of claim 1 wherein the opening of the goggle strap tab is configured to fit on the post portion of the attachment post.

3. The goggle attachment system of claim 1 wherein the stop includes a reinforcement structure extending from a surface of the stop opposite the post portion.

4. The goggle attachment system of claim 3, wherein the reinforcement structure includes at least one ridge extending along a direction from the hook portion towards the rounded pull over portion.

5. The goggle attachment system of claim 1 wherein the attachment post includes a base wider than the post portion, the base configured to be attached to a helmet.

6. The goggle attachment system of claim 5, further comprising a rail configured to be attached to a helmet, the rail having a channel configured to receive the base of the attachment post, and the base is configured to be slidably attached to the rail.

7. The goggle attachment system of claim 1 wherein the goggle strap tab comprises a tab pull.

8. The goggle attachment system of claim 7 wherein the tab pull includes a grip portion.

9. The goggle attachment system of claim 1 wherein the goggle strap tab includes a reinforcement ridge along a longitudinal direction of the goggle strap tab, the opening passing through at least a portion of the reinforcement ridge.

10. The goggle attachment system of claim 1, further comprising a helmet shell, wherein an end of the attachment post opposite the stop is attached to an exterior surface of the helmet shell.

11. The goggle attachment system of claim 10, wherein the attachment post is movably attached to the helmet shell.

12. The goggle attachment system of claim 11, wherein the attachment post is slidably coupled to a rail attached to the helmet shell.

13. The goggle attachment system of claim 1, wherein the goggle strap tab is a resilient goggle strap tab.

14. The goggle attachment system of claim 13 wherein the goggle strap tab includes one or more of a reinforcement ridge, relief portion, or combinations thereof.

15. The goggle attachment system of claim 1, wherein the attachment post is configured to be movably attached to a helmet.

16. The goggle attachment system of claim 1, wherein the opening is circular.

17. The goggle attachment system of claim 16, wherein the opening is smaller than the stop.

* * * * *